United States Patent [19]

Moore et al.

[11] Patent Number: 5,392,594
[45] Date of Patent: Feb. 28, 1995

[54] INTEGRATED PRODUCTION OF FUEL GAS AND OXYGENATED ORGANIC COMPOUNDS FROM SYNTHESIS GAS

[75] Inventors: Robert B. Moore, Allentown; William P. Hegarty, State College; David W. Studer, Wescosville; Edward J. Tirados, Easton, all of Pa.

[73] Assignee: Air Products and Chemicals, Inc., Allentown, Pa.

[21] Appl. No.: 12,092

[22] Filed: Feb. 1, 1993

[51] Int. Cl.$^6$ .................................. C01B 17/05
[52] U.S. Cl. .................. 60/39.02; 60/39.12; 423/242.4; 48/197 R
[58] Field of Search ............ 60/39.02, 39.12; 423/244.02, 244.09, 244.1, 242.4; 48/197 R, 198.3, 210

[56] References Cited

U.S. PATENT DOCUMENTS

| | | | |
|---|---|---|---|
| 2,863,527 | 12/1958 | Herbert et al. | 183/115 |
| 3,718,006 | 2/1973 | Ranke et al. | 62/17 |
| 4,031,123 | 6/1977 | Espino et al. | 260/449.5 |
| 4,277,416 | 7/1981 | Grant | 60/39.02 |
| 4,341,069 | 7/1982 | Bell et al. | 60/39.02 |
| 4,524,581 | 6/1985 | Cascone | 60/39.12 |
| 4,567,204 | 1/1986 | Mednick et al. | 518/700 |
| 4,608,818 | 9/1986 | Goebel et al. | 60/39.12 |
| 4,609,384 | 9/1986 | Ranke et al. | 55/40 |
| 4,665,688 | 5/1987 | Schiffers et al. | 60/39.07 |
| 4,824,869 | 4/1989 | Prada-Silva et al. | 518/714 |
| 4,946,477 | 8/1990 | Perka et al. | 48/197 |
| 4,957,515 | 9/1990 | Hegarty | 55/43 |

FOREIGN PATENT DOCUMENTS

| | | |
|---|---|---|
| 0353920 | 2/1990 | European Pat. Off. |
| 3609237 | 10/1986 | Germany ............ 60/39.12 |

OTHER PUBLICATIONS

*Lurgi Express Information*, pp. 1–20, Dec. 1972.
Ferrell, J. K. et al; "Regeneration of Refrigerated Methanol in Conditioning Gases From Coal"; Jun. 1987.
Underwood, R. P. et al; "Syngas Conversion to Mixed Alcohols In A Slurry Reactor"; AIChE; Jul. 1991.
Supp, E.; "Technology of Lurgi's Low Pressure Methanol Process"; *Chemtech;* Jul. 1973; pp. 430–435.

*Primary Examiner*—Richard A. Bertsch
*Assistant Examiner*—William J. Wicker
*Attorney, Agent, or Firm*—John M. Fernbacher; James C. Simmons; William F. Marsh

[57] ABSTRACT

An oxygenated organic liquid product and a fuel gas are produced from a portion of synthesis gas comprising hydrogen, carbon monoxide, carbon dioxide, and sulfur-containing compounds in a integrated feed treatment and catalytic reaction system. To prevent catalyst poisoning, the sulfur-containing compounds in the reactor feed are absorbed in a liquid comprising the reactor product, and the resulting sulfur-containing liquid is regenerated by stripping with untreated synthesis gas from the reactor. Stripping offgas is combined with the remaining synthesis gas to provide a fuel gas product. A portion of the regenerated liquid is used as makeup to the absorber and the remainder is withdrawn as a liquid product. The method is particularly useful for integration with a combined cycle coal gasification system utilizing a gas turbine for electric power generation.

30 Claims, 3 Drawing Sheets

INTEGRATED PRODUCTION OF FUEL GAS AND OXYGENATED ORGANIC COMPOUNDS FROM SYNTHESIS GAS

The U.S. Government has rights to this invention pursuant to Cooperative Agreement No. DE FC 2292 PC90548 administered by the United States Department of Energy.

FIELD OF THE INVENTION

The present invention relates to the production of oxygenated organic compounds and fuel gas from synthesis gas, and in particular to the removal of sulfur-containing compounds from the synthesis gas feed to the reactor producing the oxygenated organic compounds.

BACKGROUND OF THE INVENTION

Synthesis gas comprising hydrogen, carbon monoxide, and carbon dioxide is used for the synthesis of oxygenated organic compounds and also as a fuel gas for the generation of steam and electric power in combined cycle power generation systems. Synthesis gas generated from coal or heavy hydrocarbons typically contains sulfur compounds such as hydrogen sulfide and carbonyl sulfide which must be removed prior to use. A higher degree of sulfur removal is required for the use of synthesis gas as a chemical feedstock than as a fuel gas; this is usually the case for carbon dioxide removal as well. Carbon dioxide is also present, and removal of carbon dioxide to some degree often is required for chemical feedstocks but is required less often for fuel gas applications.

Sulfur compounds and carbon dioxide, defined as acid gases, can be removed from synthesis gas by well-known commercial processes which utilize physical absorption at elevated pressures in organic liquids such as alcohols and ethers, or which utilize chemical absorption at lower pressures by reactive liquids such as amines or inorganic alkaline solutions. Regeneration of physical absorbents is accomplished by heating, pressure reduction, or stripping with a gas lean in acid gas components, or combinations of these methods. Regeneration of chemical absorbents is usually accomplished by heating to reverse the absorption reactions and liberate the acid gas components.

The coproduction of oxygenated organic compounds and electric power from synthesis gas is a commercially attractive operation, particularly for synthesis gas produced from coal. Methanol is one organic compound of particular interest for use as a peak shaving fuel as well as a marketable product. Other organic compounds can be produced from synthesis gas via methanol with the coproduction of electric power.

Because the requirements for the removal of acid gases are more stringent for synthesis gas used as a chemical feedstock than for synthesis gas used as fuel, separate acid gas treating systems may be required in integrated plants producing organic chemicals and electric power from coal-based synthesis gas. There is a need for improved integrated acid gas removal methods for such applications which minimize capital cost, operating complexity, and energy consumption while providing appropriate low levels of acid gas contaminants in the synthesis feed gas and fuel gas. The invention disclosed in the specification below and defined in the claims which follow provides an improved integrated method for acid gas removal in such applications.

SUMMARY OF THE INVENTION

The invention is a method for producing fuel gas and a liquid product containing one or more oxygenated organic compounds from a synthesis gas comprising hydrogen, carbon monoxide, carbon dioxide, and one or more sulfur-containing compounds. The method comprises contacting a portion of the synthesis gas in an absorber system with an absorber liquid feed comprising one or more of these oxygenated organic compounds, and withdrawing a treated synthesis gas having a reduced concentration of the sulfur-containing compounds and carbon dioxide, and an absorber effluent stream containing absorbed sulfur-containing compounds and carbon dioxide. The treated synthesis gas is reacted in a catalytic reactor system to yield a reactor system liquid effluent containing the one or more oxygenated organic compounds and a stream of unreacted synthesis gas; a portion of the reactor system liquid effluent is utilized as absorber liquid feed. The absorbed sulfur-containing compounds and carbon dioxide are stripped from the absorber effluent stream by contacting the stream with at least a portion of the unreacted synthesis gas in a stripper system, and withdrawing a regenerated liquid and a stripper offgas comprising unreacted synthesis gas and sulfur-containing compounds. At least a portion of the reactor system liquid effluent is withdrawn as the liquid product. At least a portion of the regenerated liquid is combined with reactor system liquid effluent to provide the liquid feed to the absorber system. Finally, the stripper offgas and the remaining portion of synthesis gas are combined to yield the fuel gas product.

The net effect of the process of the present invention is that the sulfur-containing compounds, which poison the catalyst used in the catalytic reactor system, are bypassed around the reactor and remain in the fuel gas product at acceptable levels. The feed to the catalytic reactor system contains a sufficiently low concentration of sulfur-containing compounds. A portion of the carbon dioxide in the synthesis gas feed also is bypassed around the reactor and remains in the fuel gas product. Further treatment of the stripper offgas is not required in the present invention and the sulfur compounds and carbon dioxide therein need not be recovered. Optionally, all reactor system liquid effluent is utilized as absorber liquid feed and a portion of the regenerated liquid from the stripper system is withdrawn as the liquid product.

The oxygenated organic compounds can include methanol, mixtures of methanol and dimethyl ether, mixtures of methanol and higher alcohols, or other organic liquids depending on the specific catalytic reactor system utilized.

In an alternate embodiment, coal or heavy hydrocarbon is gasified using high pressure oxygen from an air separation system, typically by cryogenic distillation. The byproduct nitrogen at a pressure slightly higher than that required for gas turbine fuel (typically between 100 and 500 psig) is used as the stripping gas in the stripper system, the stripper offgas is combined with the untreated synthesis gas, and the resulting high pressure fuel gas is combusted in a gas turbine for the generation of electric power. In this manner the pressure energy of the nitrogen is recovered, and the combustion temperature of the gas turbine is reduced by the presence of the nitrogen thus reducing the formation of nitrogen oxides in the gas turbine system.

DETAILED DESCRIPTION OF THE INVENTION

Figure 1:
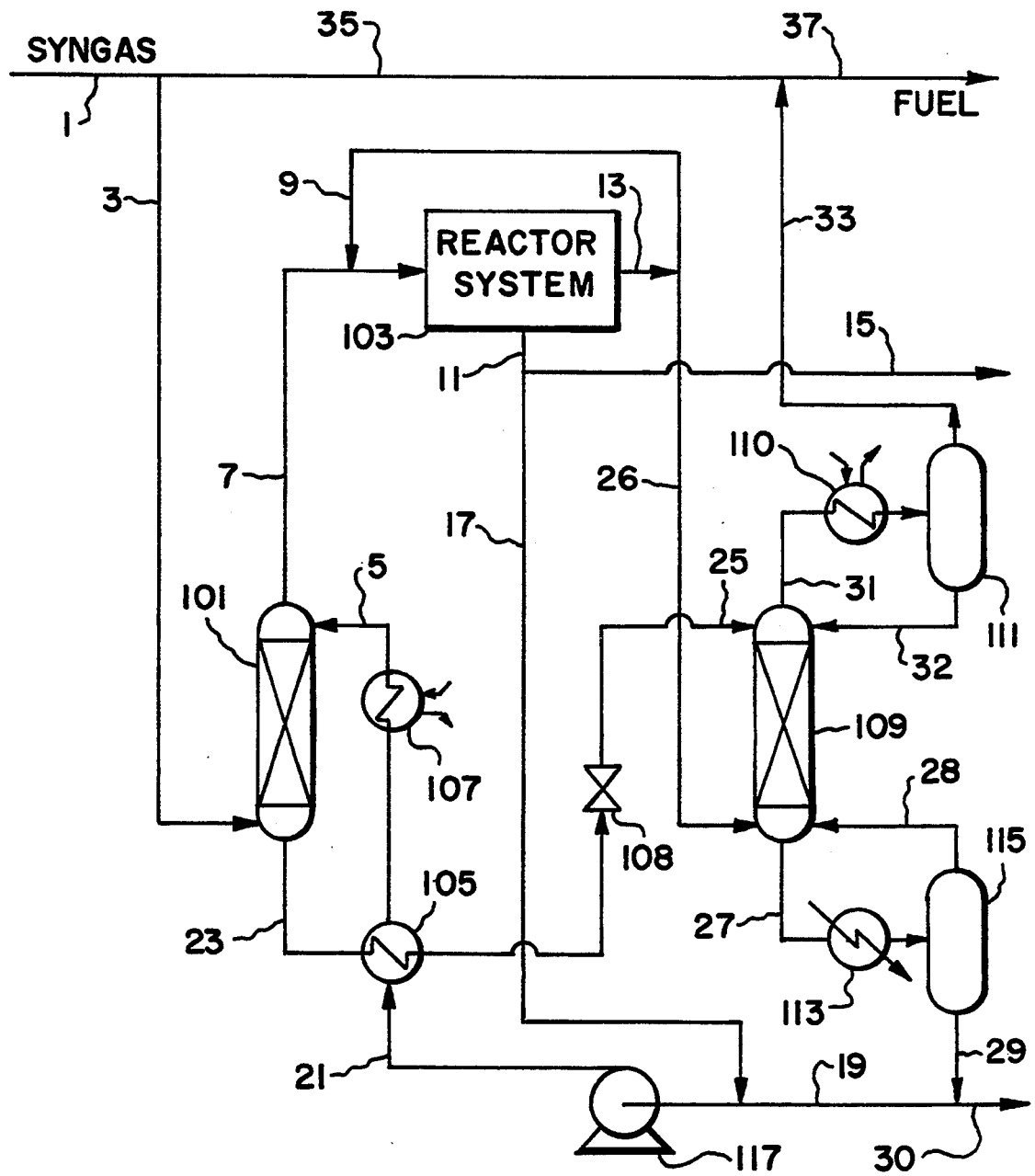
FIG. 1 is a schematic flow diagram of the method of the present invention.

A simplified flow diagram of one embodiment of the process of the present invention is given in FIG. 1. Synthesis gas 1 contains hydrogen, carbon monoxide, carbon dioxide, and sulfur-containing contaminants including hydrogen sulfide and carbonyl sulfide. This synthesis gas can be provided by the gasification of coal, petroleum coke, or heavy hydrocarbons utilizing partial oxidation or steam-oxygen gasification processes known in the art. Alternately, the synthesis gas can be produced from light hydrocarbons by steam reforming or partial oxidation as is known on the art. The total sulfur content of the synthesis gas is satisfactory for use as fuel in any type of combustion system, such as for example a gas turbine combustor; the total sulfur concentration is typically below about 100 ppmv. This level of total sulfur can be achieved by any of numerous methods known in the art, with the specific method depending on the feedstock sulfur content.

A portion 3 of this synthesis gas is compressed and cooled (not shown) by known methods and is introduced into absorber 101 where it is contacted with a cooled stream 5 of an oxygenated organic liquid which physically absorbs sulfur compounds and carbon dioxide at a pressure between about 500 and 2500 psig and a temperature between −60° and 20° F. Absorber 101 is any type of absorber known in the art having gas-liquid contacting internals such as trays, random packing, structured packing, and the like. The amount of sulfur compounds and carbon dioxide absorbed will depend on the liquid properties and the absorber operating conditions. The amount of carbon dioxide to be removed can influence the preferred absorber operating temperature; if nominal removal is acceptable, the absorber is operated for example at about 0° F. to achieve the necessary sulfur removal. If higher carbon dioxide removal is necessary to control the reaction product distribution in reactor system 103, the absorber is operated at temperatures down to −40° F. by providing additional refrigeration to cooler 107. Additional refrigeration can be supplied at the bottom of absorber 101 as required (not shown).

Organic liquid 5 contains one or more oxygenated compounds which can be produced directly by catalytic reaction of synthesis gas having the appropriate composition of hydrogen and carbon oxides; the synthesis gas contains sufficiently low concentrations of sulfur-containing compounds to prevent poisoning of the catalysts used in the synthesis gas reaction. Typically the total sulfur in the synthesis gas reactor feed must be less than 0.1 ppmv, which is significantly less than the allowable sulfur content of synthesis gas 1 as specified for use as a fuel. Absorber overhead gas 7, now containing a sufficiently low concentration of sulfur compounds and a reduced level of carbon dioxide, is warmed (not shown), optionally combined with recycle gas 9, and introduced into catalytic reactor system 103 in which synthesis gas is converted in the presence of the appropriate catalyst system into one or more oxygenated organic compounds. The oxygenated compounds are withdrawn as reactor system liquid effluent 11, and unreacted synthesis gas is withdrawn as stream 13. Optionally a portion 9 of unreacted synthesis gas 13 is recycled to reactor system 103.

A portion of reactor system liquid effluent 11 is withdrawn as liquid product 15, and the remainder 17 is combined with regenerated liquid 19. The combined liquid 21 is cooled in exchanger 105 by indirect heat exchange and cooler 107 by external refrigeration, and the cooled liquid provides oxygenated organic liquid 5 as feed to absorber 101. Additional overhead refrigeration is provided as needed (not shown). Absorber effluent stream 23 containing absorbed sulfur compounds and carbon dioxide removed from synthesis gas 3 is heated in exchanger 105, is flashed across pressure reduction valve 108, and the cooled, reduced-pressure gas/liquid stream 25 flows into stripper 109. Alternately, valve 108 can be located upstream of exchanger 105. Stripping gas 26, which is a portion of unreacted synthesis gas 13, passes countercurrently through stripper 109 and promotes the release of residual dissolved sulfur compounds and carbon dioxide from liquid stream 25. The pressure of stripping gas 26 is reduced as necessary prior to stripper 109. Stripper 109 is any type of stripping column known in the art having gas-liquid contacting internals such as trays, random packing, structured packing, and the like. The amount of sulfur compounds and carbon dioxide released will depend on the liquid properties and the stripper operating conditions. The stripper is typically operated at slightly above the gas turbine fuel gas pressure (typically between 100 and 500 psig) and at 50°–350° F. with a gas to liquid mole ratio between about 0.3 and 1.5, and yields regenerated liquid 29 containing less than 0.3 ppmv total sulfur compounds. Regenerated liquid 27 is partially vaporized in heater 113; vapor 28 from separator 115 is returned to stripper 109. A portion 19 of liquid 29 from separator 115 is combined with makeup 17, pressurized in pump 117, and returns to absorber 101 as recycle liquid 21. A small purge stream 30 is withdrawn if necessary to prevent buildup of impurities in the liquid.

Stripper offgas 31, which contains stripped sulfur compounds, carbon dioxide, remaining unreacted synthesis gas components, and some solvent, is cooled and partially condensed by refrigeration in cooler 110, and the phases are separated in separator 111. Optionally, cooler 110 and separator 111 are not needed if nominal solvent carryover is acceptable in stripper offgas 31 which is combined in fuel gas 37. Vapor 33 is combined with the remainder 35 of synthesis gas 1 to provide fuel gas product 37. Liquid 32 is returned to the top of stripper 109. The sulfur content of fuel gas 37 is below 150 ppmv, which is suitable for example as fuel for a gas turbine combustor.

The net effect the process of the present invention is that the sulfur-containing compounds, which poison the catalyst used in the catalytic reactor system 103, are bypassed around the reactor and remain in the fuel gas product 37 at acceptable levels. The feed to the catalytic reactor system 103 contains a sufficiently low concentration of sulfur-containing compounds, typically below 0.1 ppmv. Further treatment of the stripper offgas 33 is not required in the present invention and the sulfur compounds therein need not be recovered in a separate sulfur recovery system.

In an alternate mode of operation, no purge is withdrawn as stream 30, and instead liquid product 15 is subjected to a distillation step (not shown) to remove impurities from the product. Optionally, liquid product is withdrawn as a portion 30 of regenerated liquid 29 from absorber 109; all of effluent 11 from reactor system 103 flows to absorber 101 together with makeup regenerated liquid 19, and no liquid product 15 is withdrawn.

In another alternate mode of this embodiment, no liquid methanol product is withdrawn as either stream 15 or 30, and instead all methanol produced by reactor system 103 is used as a liquid fuel, preferably as a peak shaving fuel in conjunction with the combustion of fuel product 37 in a gas turbine power generation system. In this mode, all of reactor system liquid effluent 11 is used as solvent in absorber 101, and there is no regeneration of absorber effluent 25. Stripper 109 and associated equipment are eliminated, and all of unreacted synthesis gas 26 is combined with synthesis gas 35 to provide fuel gas product 37. Absorber effluent 25 is further reduced in pressure and all vapor formed (which will be chiefly carbon dioxide, hydrogen, carbon monoxide, and a very small amount of the absorbed sulfur compounds) is combined with synthesis gas 35. The resulting liquid methanol after pressure reduction contains essentially all the dissolved sulfur compounds and can be stored at near atmospheric pressure and ambient temperature. During periods of high power demand, this methanol is withdrawn for additional fuel, and the sulfur compounds therein are combusted with the methanol in the gas turbine. This mode therefore uses a simple method to protect the reactor system from sulfur contamination while providing a peak shaving fuel along with fuel gas for gas turbine operation. Complete regeneration of the methanol solvent from absorber 101 is not required.

Reactor system 103 comprises a catalytic reactor, gas/liquid product separation, and the necessary piping, pumping, compression, instrumentation, heat transfer, and other component equipment necessary to operate a catalytic reactor system. The catalyst, reactor type, and reaction chemistry are not critical to the present invention and comprise known technology. The catalyst and reactor system are selected to produce any oxygenated organic liquid of choice, which for example can be methanol, a mixture of methanol and dimethyl ether, a mixture of methanol and higher alcohols having two or more carbon atoms, or other organic compounds produced catalytically from synthesis gas containing hydrogen and carbon oxides. The specific organic compounds should have appropriate liquid vapor pressure and phase equilibrium properties for practical use as a liquid absorbent in an absorption/stripping system as described above. The catalyst used in the reactor system is sulfur-intolerant and thus requires protection against sulfur contamination by purification of the synthesis gas feed as described above.

In one mode of operation, the reactor system comprises a fixed bed, gas phase reactor containing a commercial methanol synthesis catalyst. Methanol is produced from a portion of the synthesis gas using such a reactor system as is well known in the art. In an alternate and preferred mode of operation, the reactor system comprises a liquid phase reactor in which a powdered methanol synthesis catalyst is slurried in an inert liquid and the synthesis gas is reacted in the resulting three phase reactor to yield methanol. This process is known in the art as described in U.S. Pat. Nos. 4,031,123 and 4,567,204, and these patents are incorporated herein by reference. In both modes, methanol is the product as well as the absorber medium for removal of sulfur compounds, and the remaining synthesis gas and stripper offgas gas are combined to comprise the fuel product as shown in FIG. 1.

In another embodiment, the present invention comprises the production of a mixture of methanol and dimethyl ether from synthesis gas using a gas phase fixed bed reactor or preferably a liquid phase reactor system. In the liquid phase reactor, a mixture of powdered methanol synthesis catalyst and methanol dehydration catalyst is suspended in an inert liquid and the synthesis gas is contacted with the catalyst in the resulting three phase reactor system. This mode is described in allowed U.S. patent application Ser. No. 07/873,493, filed Apr. 23, 1992, which is incorporated herein by reference. The liquid product composition depends on the relative amounts of synthesis and dehydration catalysts in the reactor. The liquid product 11 is used directly as makeup for the absorber liquid feed for sulfur removal as described above, and the remaining synthesis gas and stripper offgas gas are combined to yield fuel product 37 as shown in FIG. 1. Because dimethyl ether is quite volatile compared to methanol, it is preferable to withdraw the major portion of reactor effluent 11 as liquid product 15, and use the small liquid stream 17 as makeup to absorber 101. Most dimethyl ether in absorber effluent 25 will be stripped and incorporated into fuel gas 37; this is not a problem since the small amount of dimethyl ether will combust easily with fuel gas 37. The loss of dimethyl ether product in this manner will be acceptably small, and allows the convenient use of reactor liquid effluent 17 as absorber makeup. The liquid in absorber 101 thus will be essentially methanol with a small concentration of dimethyl ether added in makeup stream 17.

In another embodiment, similar to that described above for the production of a methanol-dimethyl ether mixture, an alternate catalyst comprising alkali-promoted metal oxides is used which converts the synthesis gas into a mixture of methanol and higher alcohols having two or more carbon atoms. This mixture is utilized both as a product and as sulfur absorption medium in a manner similar to the embodiments described above. Higher alcohols, in particular ethanol, $C_3$ alcohols, and $C_4$ alcohols but also including higher boiling alcohols, have favorable physical properties for use as a liquid absorbent for the operation of an absorber-stripper system at reasonable operating conditions. Various catalysts for producing mixed alcohols from synthesis gas are known in the art as described for example in U.S. Pat. No. 4,824,869 which is incorporated herein by reference. The catalyst is preferably used in a powdered form suspended in an inert liquid in a liquid phase reactor. Alternately, the catalyst can be used in a fixed-bed reactor in pellet form. In this embodiment, reactor liquid product 11 (FIG. 1) contains methanol and alcohols less volatile than methanol, and a portion of product 11 is used as makeup 17 for absorber 101. At steady state operation, recirculating liquid 5 to absorber 101 will contain a lower concentration of methanol than reactor liquid product 11, since some methanol will be lost in stripper offgas 33 at the stripper conditions necessary to regenerate the recirculating absorber liquid 19. The methanol in stripper offgas 33 becomes part of fuel gas product 37, and the presence of methanol therein is not a problem since methanol is readily combustible with the other fuel components present. The net effect is that the major portion of absorber makeup 17 is added to recirculating absorber liquid 19 to replace liquid withdrawn as purge 30, and the small remaining portion of absorber makeup 17 eventually enters fuel gas 37 via stripper offgas 33. As in the alternate embodiment described above, the import and storage of makeup solvent is not required as would be the case with a standalone commercially-available physical solvent absorption system, since the product of reactor system 103 is used as the absorber liquid makeup.

Figure 2:
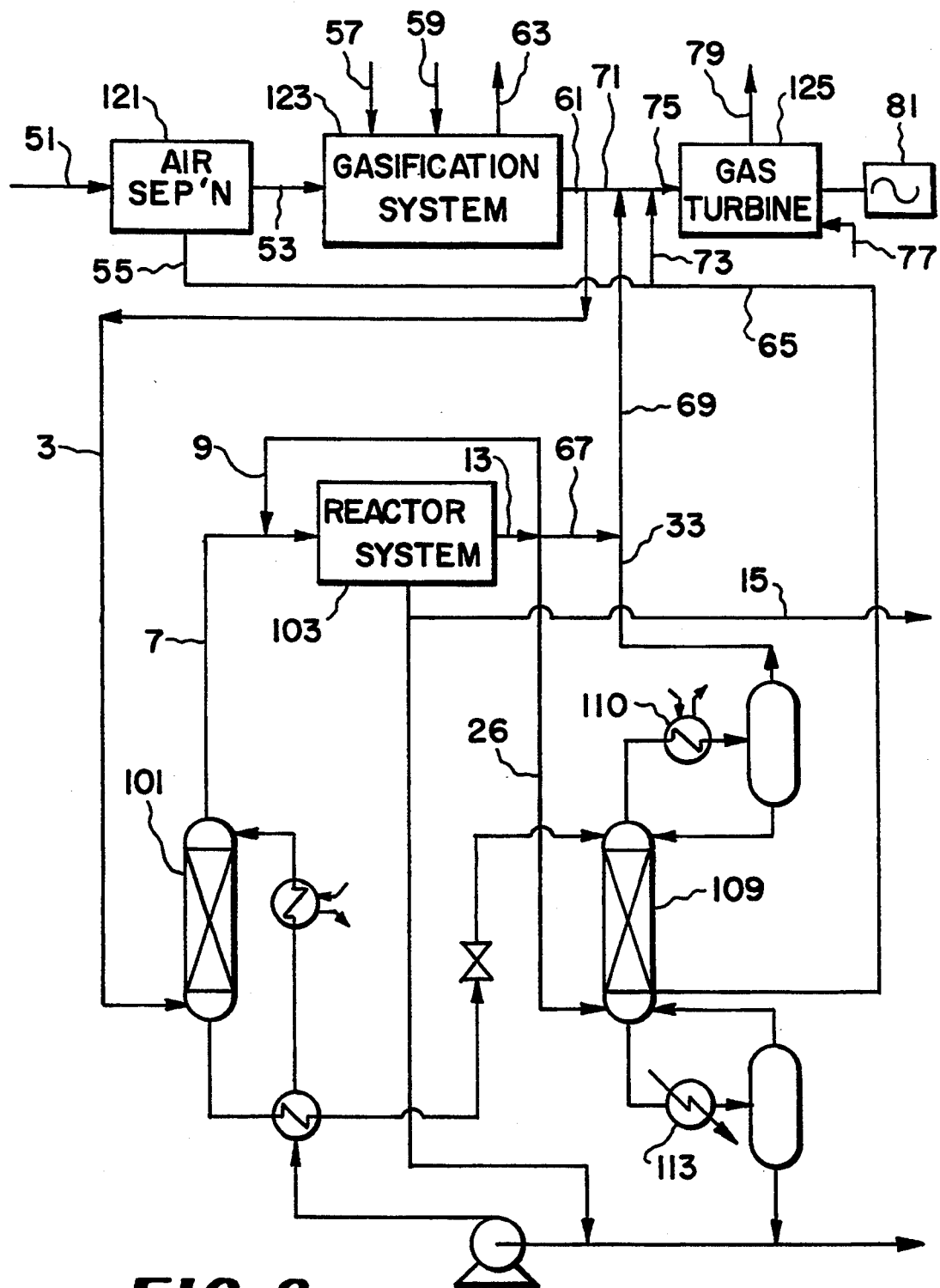
FIG. 2 is a schematic flow diagram of an alternate embodiment of the method of the present invention.

An alternate embodiment of the present invention is shown in the schematic flow diagram of FIG. 2. Air 51 is separated in air separation unit 121 to produce oxygen stream 53 containing at least 90 vol % oxygen and nitrogen stream 55 containing at least 97 vol % nitrogen. Typically, unit 121 is a cryogenic air separation system operating between 70 and 300 psig. Oxygen and nitrogen are provided at ambient temperature, and at pressures of 200 to 1300 psig for oxygen and 100 to 500 psig for nitrogen. Oxygen 53, carbonaceous feed 57, and optionally steam 59 are reacted in gasification system 123 at 200 to 1300 psig to produce synthesis gas 61 comprising hydrogen, carbon monoxide, carbon dioxide, and sulfur-containing compounds including hydrogen sulfide and carbonyl sulfide. System 123 can comprise partial oxidation or steam-oxygen gasification processes known in the art to gasify coal, petroleum coke, or heavy hydrocarbons. Alternately, synthesis gas can be produced in system 123 from light hydrocarbons by steam reforming or partial oxidation as is known in the art. Particulates, condensate, and optionally some of the sulfur compounds are removed from the synthesis gas within system 123 by known methods to yield contaminant reject stream 63. The total sulfur content of synthesis gas 61 is specified for use as a fuel in any type of combustion system, such as for example a gas turbine combustor; the total sulfur concentration is typically below about 100 ppmv. This level of total sulfur can be achieved by any of numerous methods known in the art, with the specific method depending on the feedstock sulfur content and other factors. A portion 3 of synthesis gas 61 is treated in absorber 101 for further sulfur removal and used to synthesize selected oxygenated organic compounds as described above in connection with FIG. 1. At least a portion of nitrogen stream 55 is used as stripping gas 65 in stripper 109. Optionally, a portion of unreacted synthesis gas 26 from reactor system 103 can be used as additional stripping gas if needed. Stripper offgas 33 is combined with remaining unreacted synthesis gas 67; the combined stream 69 is further combined with remaining synthesis gas 71 and optionally at least a portion of remaining nitrogen 73 to yield gas turbine fuel 75. Fuel 75 is combusted with air 77 in gas turbine system 125 to generate steam 79 and electric power 81.

The use of nitrogen 65 as a stripping gas has several advantages in this embodiment of the invention. First, the nitrogen in the stripper offgas is included in fuel gas 75 to turbine 125, which recovers the pressure energy of the nitrogen and thereby increases the overall energy efficiency of the system of FIG. 2. In addition, the use of nitrogen as stripping gas may reduce the amount of heat required at heater 113 to provide boilup for stripper 109 by allowing higher stripping rates than those attainable by the use of unreacted synthesis gas. The use of nitrogen for stripping, whereby the nitrogen is included in fuel gas 75, also lowers the combustion temperature in the gas turbine combustor which reduces the generation of nitrogen oxides.

The present invention has distinct advantages compared with the use of commercially available physical solvent absorption systems. Since the solvent of the present invention contains the compounds formed in reactor system 103, some solvent carryover in treated synthesis gas 7 from absorber 101 is acceptable. Additional refrigeration to remove all solvent from synthesis gas 7 is not required. In addition, import and storage of makeup solvent is not required as would be the case with a standalone commercially-available physical solvent absorption system, since the product of reactor system 103 is used as the absorber liquid and makeup. Further, the solvent components which are products of reactor system 103 can be used as peaking fuel in conjunction with fuel gas 37. Thus some solvent carryover in stripper offgas 33 is not a problem since the components are acceptable fuel components and are readily replaced in the absorber liquid by reactor product 13; in addition, the refrigeration requirement for cooler 110 can be minimized. The use of nitrogen as a stripping gas would lower the heat requirement for heater 113 as earlier noted. Other advantages of using nitrogen as a stripping gas have been discussed above.

EXAMPLE 1

Figure 3:
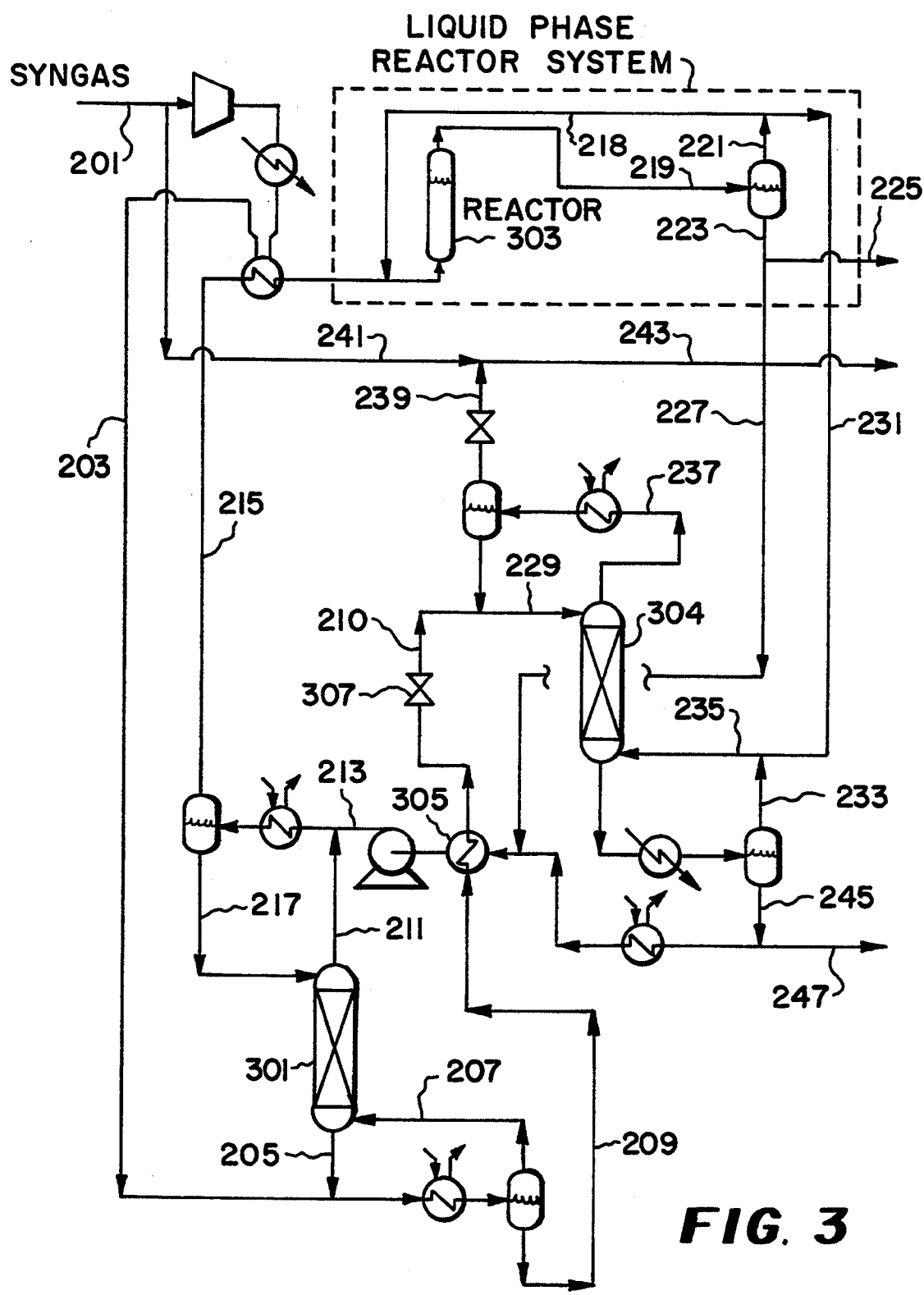
FIG. 3 is a specific application of the present invention used in conjunction with the Examples presented herein.

A process heat and material balance was calculated for the process of FIG. 1 in which methanol is the synthesized organic product which as well as the solvent for sulfur removal. A more detailed flowsheet for this example is given in FIG. 3. Synthesis gas 201 is obtained by coal gasification with preliminary gas cleanup and contains 50 ppmv total of hydrogen sulfide plus carbonyl sulfide and 13.2 mol % carbon dioxide. A portion 203 (204 of synthesis gas 201) is compressed and cooled to 1200 psia and 30° F., and this portion 203 is combined with sulfur-rich methanol stream 205 from absorber 301. The combined stream is cooled and separated into vapor 207, which is fed to absorber 301, and liquid 209, which is heated against regenerated stripper bottoms in exchanger 305 and flashed to 350 psia across valve 307. Synthesis gas and absorbent liquid are contacted at 0° F. in absorber 301 wherein essentially all of the sulfur compounds and some of the carbon dioxide are absorbed. Offgas 211 is combined with regenerated methanol solvent 213, cooled, and separated into purified synthesis gas reactor feed 215 and fresh liquid absorbent 217 which flows into absorber 301. Reactor feed 215 at 0° F. which contains 0.07 ppmv total sulfur compounds is heated to 100° F., combined with recycled synthesis gas 218, and flows into synthesis reactor 303. The reactor contains a powdered form of the copper-based methanol synthesis catalyst BASF S3-86 suspended in the inert hydrocarbon Drakeol 10, and operates at 1060 psia and 482° F. Reactor effluent 219 is cooled, partially condensed, and separated into unreacted synthesis gas 221 and methanol liquid product 223. A major portion 225 is withdrawn as a methanol product and the remainder 227 provides liquid absorbent makeup for absorber 301.

Sulfur-containing methanol stream 210 is combined with overhead condensate from stripper 304 to yield absorber liquid feed 229. The remainder 231 of unreacted synthesis gas 221 is combined with boilup vapor and the combined stream strips the absorbed sulfur compounds and part of the carbon dioxide from the liquid methanol absorbent in stripper 304 which operates at overhead conditions of 350 psia and 61° F. Stripper offgas 237 is cooled to condense vaporized methanol, and the vapor which contains unreacted synthesis gas, stripped carbon dioxide, and stripped sulfur compounds is combined with the remainder 241 of synthesis gas 201 to yield fuel gas 243 which is suitable for gas turbine fuel. Stripper bottoms stream 245 is cooled, combined with reactor liquid product 227, and pressurized to provide regenerated methanol solvent 213. A small blowdown stream 247 is withdrawn to purge the system.

A summary of the key stream properties of this Example is given in Table 1. It is seen that diverting 204 of the flow of synthesis gas 201 as

EXAMPLE 2

The system of Example 1 is operated at the same process conditions except that absorber 301 is operated at −40° F. This yields a 91.44 removal of carbon dioxide from synthesis gas 203 by absorber 301, which in turn yields methanol product 225 containing 0.15 mol % water. The water content of the methanol product from reactor 303 thus can be controlled by operating the absorber 301 at the appropriate temperature.

Thus the method of the present invention allows the integrated production of fuel gas and an oxygenated organic liquid product from synthesis gas comprising hydrogen, carbon monoxide, carbon dioxide, and sulfur-containing compounds. The net effect of the process of the present invention is that the sulfur-containing

TABLE 1

STREAM PROPERTIES FOR EXAMPLE 1

| STREAM NUMBER | 201 | 203 | 205 | 209 | 213 | 215 | 217 | 221 | 223 | 225 | 243 | 247 |
|---|---|---|---|---|---|---|---|---|---|---|---|---|
| PRESSURE, PSIA | 200 | 1200 | 1200 | 1200 | 1200 | 1200 | 1060 | 1060 | 1060 | 1060 | 200 | 350 |
| TEMPERATURE, °F. | 80 | 30 | 9 | 0 | 22 | 0 | 100 | 100 | 100 | 100 | 75 | 233 |
| TOTAL FLOW, MOL/HR | 19500 | 3900 | 3057 | 3102 | 2741 | 3539 | 3539 | 5440 | 557 | 552 | 17852 | 14 |
| COMPOSITION, MOL % (PPM) | | | | | | | | | | | | |
| CARBON MONOXIDE | 48.2 | 48.2 | 1.1 | 1.1 | 0.8 | 52.8 | 69.6 | 69.6 | 1.9 | 1.9 | 49.4 | 0.7 |
| HYDROGEN | 38.0 | 38.0 | 0.4 | 0.4 | 0.1 | 41.6 | 20.2 | 20.02 | 0.3 | 0.3 | 35.4 | 0.1 |
| CARBON DIOXIDE | 13.2 | 13.2 | 10.1 | 11.5 | 0.6 | 4.9 | 8.0 | 8.0 | 3.2 | 3.2 | 14.3 | 0.5 |
| HYDROGEN SULFIDE | (20) | (20) | (9) | (25) | (0.04) | (0.01) | — | — | — | — | (22) | (0.03) |
| CARBONYL SULFIDE | (30) | (30) | (19) | (38) | (0.05) | (0.06) | — | — | — | — | (33) | (0.05) |
| NITROGEN | 0.6 | 0.6 | — | — | — | 0.7 | 1.3 | 1.3 | — | — | 0.7 | — |
| WATER | — | — | 2.2 | 2.2 | 2.5 | — | — | — | 0.4 | 0.4 | — | 2.5 |
| METHANOL | — | — | 86.1 | 84.8 | 96.0 | — | 0.9 | 0.9 | 94.1 | 94.1 | — | 96.0 | reactor feed, with a reactor recycle 217 to fresh feed 215 molar ratio of 1:1, increases the concentration of sulfur compounds in final fuel gas 243 by only about 10%. The net mass flow of sulfur in fuel gas 243, however, is essentially the same as in synthesis gas 201, since essentially all sulfur removed from reactor fresh feed 215 is rejected in stream 239. This illustrates a key feature of the present invention, namely, the simple and integrated method for preventing catalyst poisoning in reactor 303 without the need for complex standalone sulfur removal and recovery systems. As a larger fraction of synthesis gas 201 is taken for reactor feed, the net flow of fuel gas 243 will decrease and the concentration of sulfur compounds therein will increase. The net mass flow of sulfur in the fuel gas, however, will be essentially constant. For a fixed ratio of synthesis gas 203 (reactor feed) to synthesis gas 243 (fuel), the sulfur concentration in synthesis gas 201 should be set such that the mass of sulfur in fuel 243 allows the combustion step using this fuel to meet the appropriate flue gas sulfur emission regulations.

At these operating conditions the process of the present invention removes 66% of the carbon dioxide from synthesis gas 203 to provide reactor feed 215. Essentially all of this carbon dioxide is recovered and included in fuel gas product 243 via stripper overhead 239. By this feature of the present invention, a major portion of the pressure energy of the carbon dioxide can be recovered when the fuel is combusted in a gas turbine as in FIG. 2. Carbon dioxide in the feed to reactor 303 is converted in part to water via the reverse water gas shift reaction; methanol product 225 thus contains 0.4 mol % water. If lower water content is required, a higher level of carbon dioxide removal can be achieved in absorber 301 as described in the following Example.

compounds, which poison the catalyst used in the catalytic reactor system, are bypassed around the reactor and remain in the fuel gas product at acceptable levels. The feed to the catalytic reactor system, after contacting in an absorber with a liquid comprising the same oxygenated organic compounds produced in the reactor system, thus contains a sufficiently low concentration of sulfur-containing compounds. Further treatment of the stripper offgas is not required and the sulfur compounds therein need not be recovered. In addition, a portion of the oxygenated organic liquid product is used directly as solvent makeup for the absorber, so that import and storage of makeup solvent is not necessary. A small loss of solvent in the stripper offgas is not a problem when the solvent components are readily combustible, since the stripper offgas is combined with synthesis gas and the combined gas used as fuel.

In the alternate embodiment described above, coal or heavy hydrocarbon is gasified using high pressure oxygen from an air separation system. The byproduct nitrogen at a pressure between 100 and 500 psig is used as the stripping gas in the stripper system, the stripper offgas is combined with the untreated synthesis gas, and the resulting high pressure fuel gas is combusted in a gas turbine for the generation of electric power. In this manner the pressure energy of the nitrogen is recovered, and the combustion temperature of the gas turbine is reduced by the presence of the nitrogen thus reducing the formation of nitrogen oxides in the gas turbine system.

The essential characteristics of the present invention are described completely in the foregoing disclosure. One skilled in the art can understand the invention and make various modifications thereto without departing from the basic spirit thereof, and without departing from the scope and range of equivalents of the claims which follow.

We claim:

1. A method for producing fuel gas and a liquid product containing one or more oxygenated organic compounds from a synthesis gas comprising hydrogen, carbon monoxide, carbon dioxide, and one or more sulfur-containing compounds, said method comprising:
   a) contacting a portion of said synthesis gas in an absorber system with an absorber liquid feed comprising one or more of said oxygenated organic compounds, wherein at least a portion of said one or more sulfur-containing compounds and carbon dioxide is physically absorbed by said absorber liquid feed, and withdrawing therefrom a treated synthesis gas having reduced concentrations of said sulfur-containing compounds and carbon dioxide, and an absorber effluent stream containing absorbed sulfur-containing compounds and carbon dioxide;
   b) reacting said treated synthesis gas in a catalytic reactor system to yield a reactor system liquid effluent comprising said one or more oxygenated organic compounds and a stream of unreacted synthesis gas, and utilizing a portion of said reactor system liquid effluent in said absorber liquid feed;
   c) stripping said absorbed sulfur-containing compounds and carbon dioxide from said absorber effluent stream by contacting the stream with at least a portion of said unreacted synthesis gas in a stripper system, and withdrawing therefrom a regenerated liquid and a stripper offgas comprising unreacted synthesis gas, carbon dioxide, and sulfur-containing compounds;
   d) withdrawing at least a portion of said reactor system liquid effluent as said liquid product;
   e) combining at least a portion of said regenerated liquid with said portion of reactor system liquid effluent to form the absorber liquid feed prior to said absorber system; and
   f) combining said stripper offgas and the remaining portion of said synthesis gas to yield said fuel gas.

2. The method claim 1 which further comprises withdrawing a portion of said regenerated liquid as a purge stream.

3. The method of claim 1 which further comprises recycling another portion of said unreacted synthesis gas as feed to said catalytic reactor system.

4. The method of claim 1 wherein said catalytic reactor system and said absorber system are operated in the pressure range between 500 and 2500 psig.

5. The method of claim 1 which further comprises treating said liquid product by distillation to remove additional impurities therefrom.

6. A method for producing fuel gas and a liquid product containing one or more oxygenated organic compounds from a synthesis gas comprising hydrogen, carbon monoxide, carbon dioxide, and one or more sulfur-containing compounds, said method comprising:
   a) contacting a portion of said synthesis gas in an absorber system with an absorber liquid feed comprising one or more of said oxygenated organic compounds, wherein at least a portion of said one or more sulfur-containing compounds and carbon dioxide is physically absorbed by said absorber liquid feed, and withdrawing therefrom a treated synthesis gas having a reduced concentration of said sulfur-containing compounds and carbon dioxide, and an absorber effluent stream containing absorbed sulfur-containing compounds and carbon dioxide;
   b) reacting said treated synthesis gas in a catalytic reactor system to yield a reactor system liquid effluent comprising said one or more oxygenated organic compounds and a stream of unreacted synthesis gas, wherein at least a portion of said reactor system liquid effluent is utilized as said absorber liquid feed;
   c) stripping said absorbed sulfur-containing compounds and carbon dioxide from said absorber effluent stream by contacting the stream with at least a portion of said unreacted synthesis gas in a stripper system, and withdrawing therefrom a regenerated liquid and a stripper offgas comprising unreacted synthesis gas, carbon dioxide, and sulfur-containing compounds;
   d) withdrawing a portion of said regenerated liquid as said liquid product;
   e) combining another portion of said regenerated liquid with said absorber liquid feed prior to said absorber system; and
   f) combining said stripper offgas and the remaining portion of said synthesis gas to yield said fuel gas.

7. The method of claim 6 wherein the absorber system is operated in the temperature range of $-60°$ to $0°$ F.

8. The method of claim 1 wherein said one or more oxygenated organic compounds comprise methanol.

9. The method of claim 8 wherein said catalytic reactor system contains a copper-based methanol synthesis catalyst.

10. The method of claim 9 wherein said catalytic reactor system comprises a liquid phase reactor containing a powdered copper-based methanol synthesis catalyst suspended in an inert liquid.

11. The method of claim 1 wherein said one or more oxygenated organic compounds comprise methanol and one or more additional oxygenated organic compounds having two or more carbon atoms.

12. The method of claim 11 wherein said catalytic reactor system contains a copper-based methanol synthesis catalyst and an acidic methanol dehydration catalyst by which a portion of said treated synthesis gas is converted to methanol and dimethyl ether.

13. The method of claim 12 wherein said catalytic reactor system comprises a liquid phase reactor containing a powdered copper-based methanol synthesis catalyst and a powdered acidic methanol dehydration catalyst suspended in an inert liquid.

14. The method of claim 11 wherein said one or more additional oxygenated organic compounds comprise higher alcohols containing two or more carbon atoms.

15. The method of claim 14 wherein said catalytic reactor system contains a catalyst which promotes the reaction of a portion of said treated synthesis gas to yield methanol and one or more higher alcohols containing two or more carbon atoms.

16. The method of claim 15 wherein said catalytic reactor system comprises a liquid phase reactor containing a powdered form of said catalyst suspended in an inert liquid.

17. A method for producing fuel gas and a liquid product containing one or more oxygenated organic compounds from a synthesis gas comprising hydrogen, carbon monoxide, carbon dioxide, and one or more sulfur-containing compounds, said method comprising:
   a) contacting a portion of said synthesis gas in an absorber system with an absorber liquid feed comprising one or more of said oxygenated organic compounds, wherein at least a portion of said one or more sulfur-containing compounds and carbon dioxide is physically absorbed by said absorber liquid feed, and withdrawing therefrom a treated synthesis gas having a reduced concentration of said sulfur-containing compounds and carbon dioxide, and an absorber effluent stream containing absorbed sulfur-containing compounds and carbon dioxide;

b) reacting said treated synthesis gas in a catalytic reactor system to yield a reactor system liquid effluent comprising said one or more oxygenated organic compounds and a stream of unreacted synthesis gas, wherein at least a portion of said reactor system liquid effluent is utilized as said absorber liquid feed;

c) stripping said absorbed sulfur-containing compounds and carbon dioxide from said absorber effluent stream by contacting the stream with at least a portion of said unreacted synthesis gas in a stripper system, and withdrawing therefrom a regenerated liquid and a stripper offgas comprising unreacted synthesis gas, carbon dioxide, and sulfur-containing compounds;

d) withdrawing a portion of said regenerated liquid as said liquid product;

e) combining another portion of said regenerated liquid with said absorber liquid feed prior to said absorber system; and f) combining said stripper offgas and the remaining portion of said synthesis gas to yield said fuel gas.

18. The method of claim 17 which further comprises recycling another portion of said unreacted synthesis gas as feed to said catalytic reactor system.

19. A method for producing fuel gas and a liquid product containing one or more oxygenated organic compounds comprising:

a) separating air in an air separation system at a pressure between 70 and 300 psig to yield oxygen and nitrogen products;

b) gasifying a carbonaceous feedstock at a pressure between 200 and 1300 psig in a partial oxidation or a steam-oxygen gasification system using said oxygen product as an oxidant to produce a synthesis gas comprising hydrogen, carbon monoxide, carbon dioxide, and one or more sulfur-containing compounds;

c) contacting a portion of said synthesis gas in an absorber system with an absorber liquid feed comprising one or more of said oxygenated organic compounds, and withdrawing therefrom a treated synthesis gas having a reduced concentration of said sulfur-containing compounds and carbon dioxide, and an absorber effluent stream containing absorbed sulfur-containing compounds and carbon dioxide;

d) reacting said treated synthesis gas in a catalytic reactor system to yield a reactor system liquid effluent comprising said one or more oxygenated organic compounds and a stream of unreacted synthesis gas;

e) stripping said absorbed sulfur-containing compounds and carbon dioxide from said absorber effluent stream by contacting the stream with at least a portion of said nitrogen product in a stripper system, and withdrawing therefrom a regenerated liquid stream and a stripper offgas comprising nitrogen, carbon dioxide, and sulfur-containing compounds;

f) combining said regenerated liquid stream with a portion of said reactor system liquid effluent to provide said absorber liquid feed;

g) withdrawing another portion of said reactor system liquid effluent as said liquid product; and h) combining said stripper offgas and the remaining portion of said synthesis gas to yield said fuel gas.

20. The method of claim 19 which further comprises combusting a portion of said liquid product comprising said one or more oxygenated organic compounds as fuel in said gas turbine system.

21. The method of claim 19 which further comprises combining at least a portion of said unreacted synthesis gas with said fuel gas.

22. The method of claim 19 which further comprises recycling another portion of said unreacted synthesis gas as feed to said catalytic reactor system.

23. The method of claim 19 which further comprises cooling said absorber liquid feed prior to said absorber system such that said absorber operates in the temperature range of $-60°$ to $20°$ F.

24. The method of claim 19 which further comprises combusting said fuel gas in a gas turbine whereby the pressure energy of said nitrogen is recovered, and whereby the combustion temperature of said gas turbine is reduced by the presence of said nitrogen thus reducing the formation of nitrogen oxides in said gas turbine system.

25. The method of claim 20 which further comprises combining another portion of said nitrogen product with said fuel gas prior to combustion in said gas turbine.

26. The method of claim 19 wherein said one or more oxygenated organic compounds comprise methanol.

27. The method of claim 26 wherein said catalytic reactor system contains a copper-based methanol synthesis catalyst.

28. The method of claim 27 wherein said catalytic reactor system comprises a liquid phase reactor containing powdered copper-based methanol synthesis catalyst suspended in an inert liquid.

29. A method for producing a fuel gas product and a liquid fuel product containing one or more oxygenated organic compounds from a synthesis gas comprising hydrogen, carbon monoxide, carbon dioxide, and one or more sulfur-containing compounds, said method comprising:

a) contacting a portion of said synthesis gas in an absorber system with an absorber liquid feed comprising one or more of said oxygenated organic compounds, wherein at least a portion of said one or more sulfur-containing compounds and carbon dioxide is physically absorbed by said absorber liquid feed, and withdrawing therefrom a treated synthesis gas having reduced concentrations of said sulfur-containing compounds and carbon dioxide, and an absorber effluent stream containing absorbed sulfur-containing compounds and carbon dioxide at a superatmospheric pressure;

b) reacting said treated synthesis gas in a catalytic reactor system to yield a reactor system liquid effluent comprising said one or more oxygenated organic compounds and a stream of unreacted synthesis gas, and utilizing said reactor system liquid effluent as said absorber liquid feed;

c) combining said stream of unreacted synthesis gas with the remaining portion of said synthesis gas to provide said fuel gas product; and d) withdrawing said absorber effluent stream to provide said liquid fuel product at said superatmospheric pressure.

30. The method of claim 29 which further comprises reducing the pressure of said liquid fuel product below said superatmospheric pressure, thereby releasing dissolved gases, combining the released gases with said fuel gas product, and withdrawing a reduced-pressure liquid fuel product.

* * * * *